United States Patent
Yamamoto (10) Patent No.: US 9,927,432 B2
(45) Date of Patent: Mar. 27, 2018

(54) BIOSENSOR HAVING DECOUPLED CAPTURE CHAMBER AND DETECTION CHAMBER, USING PARTICLE AGGREGATION AND SIZE-SEPARATION

(71) Applicant: KONICA MINOLTA LABORATORY U.S.A., INC., San Mateo, CA (US)

(72) Inventor: Noriaki Yamamoto, Foster City, CA (US)

(73) Assignee: KONICA MINOLTA LABORATORY U.S.A., INC., San Mateo, CA (US)

( * ) Notice: Subject to any disclaimer, the term of this patent is extended or adjusted under 35 U.S.C. 154(b) by 293 days.

(21) Appl. No.: 14/737,195

(22) Filed: Jun. 11, 2015

(65) Prior Publication Data

US 2015/0362485 A1     Dec. 17, 2015

Related U.S. Application Data (60) Provisional application No. 62/012,007, filed on Jun. 13, 2014.

(51) Int. Cl.
    *B01L 3/00*     (2006.01)
    *G01N 33/543*   (2006.01)

(52) U.S. Cl.
    CPC .. *G01N 33/54366* (2013.01); *B01L 3/502753* (2013.01); *G01N 33/54313* (2013.01); *B01L 3/502738* (2013.01); *B01L 2200/0631* (2013.01); *B01L 2300/0681* (2013.01); *B01L 2300/088* (2013.01);
    (Continued)

(58) Field of Classification Search
    None
    See application file for complete search history.

(56) References Cited

U.S. PATENT DOCUMENTS

2011/0236264 A1* 9/2011 Rajagopal ......... B01L 3/502753
                                                         422/82.07
2011/0312518 A1* 12/2011 Davis ................ B01L 3/502761
                                                             506/9

FOREIGN PATENT DOCUMENTS

WO      2010/125932 A1   11/2010

OTHER PUBLICATIONS

Mok et al., "Digital microfluidic assay for protein detection", Proceedings of the National Academy of Sciences, Feb. 11, 2014, vol. 111, No. 6, pp. 2110-2115.

* cited by examiner

*Primary Examiner* — Rebecca L Martinez
(74) *Attorney, Agent, or Firm* — Chen Yoshimura LLP (57) ABSTRACT

A biosensor using a decoupled microfluidic device, which has a capture chamber and a detection chamber separate from and in fluid communication with each other. The sensing method is based on particle aggregation via homogeneous reactions, by employing microparticles having antibodies on their surfaces which can form aggregates through antigen mediation. Either size-separation or magnetic based separation is used to separate aggregates from single microparticles; the aggregates are later dissociated and the resulting single microparticles are counted to measure the amount of the antigen. Another biosensor uses a decoupled microfluidic device with a capture chamber and a detection chamber, and a 3-D structure in the capture camber to increase immobilized antibody concentration. Immunoreaction efficiency is improved by increasing the number of antibody per reaction volume in the capture chamber.

4 Claims, 11 Drawing Sheets

(52) U.S. Cl.
CPC .............. *B01L 2300/0864* (2013.01); *B01L 2300/0867* (2013.01); *B01L 2300/0877* (2013.01)

BIOSENSOR HAVING DECOUPLED CAPTURE CHAMBER AND DETECTION CHAMBER, USING PARTICLE AGGREGATION AND SIZE-SEPARATION

BACKGROUND OF THE INVENTION

Field of the Invention

This invention relates to biosensor for point-of-care (POC) diagnostics, and in particular, it relates to a biosensor using a decoupled microfluidic device that employs particle aggregation and size-separation.

Description of Related Art

High-sensitive, rapid and inexpensive biosensors, i.e. sensors for detecting biomolecules, such as DNA or protein sensors, are desired for point-of-care (POC) diagnostics. In conventional biosensors, the capture step and the detection step are coupled to each other. In the capture step, the biomolecules to be detected are captured by capture agents in a chamber of the biosensor; in the detection step, the captured biomolecules are detected. In the case of such capture and detection coupled biosensor, there is often a tradeoff between one (e.g. capture) and the other (e.g. detection) and both cannot be optimized simultaneously.

A team at Stanford Genome Technology Center developed an ultra-sensitive electronic microfluidic technique, referred to as "decoupled" digital detection. Using this technique, the team has demonstrated an attomolar level limit of detection (LOD) with palm-top size devices. See Mok et al., Digital microfluidic assay for protein detection, Proc Natl Acad Sci USA 2014 Feb. 11; 111(6):2110-5 ("Mok et al., PNAS 2014"); see also US 2011/0312518 A1. In this decoupled system, the capture chamber and the detection chamber are completely separated physically, which offers a large degree of flexibility in tailoring each chamber. Noises due to non-specific binding can be reduced, resulting in increased sensitivity. However, this technology is slow, requiring a relatively long time for the capture reaction (on the order of one hour) due to the low concentration of capture antibodies and the small volume of the capture chamber.

SUMMARY

The present invention is directed to a biosensor and related method that substantially obviates one or more of the problems due to limitations and disadvantages of the related art.

An object of the present invention is to improve reaction speed of the decoupled biosensor.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and/or other objects, as embodied and broadly described, the present invention provides a microfluidic device forming a biosensor, which includes: a capture chamber; a detection chamber separate from and in fluid communication with the capture chamber, the detection chamber having a detection device for detecting single microparticles passing through the detection chamber; and a separation mechanism located in the capture chamber or between the capture chamber and the detection chamber, for separating aggregations of the microparticles and single microparticles.

In another aspect, the present invention provides a microfluidic device forming a biosensor, which includes: a capture chamber; a detection chamber in fluid communication with the capture chamber, the detection chamber having a detection device for detecting single microparticles passing through the detection chamber; and a magnetic based separation mechanism located in the capture chamber, including a magnet for generating a magnetic field in the capture chamber.

In yet another aspect, the present invention provides a method for detecting an antigen using a biosensor, the biosensor having a capture chamber and detection chamber which are separate from and in fluid communication with each other, the method including: applying a sample in the capture chamber, the sample containing the antigen and microparticles having antibodies immobilized on their surfaces; allowing the microparticles to form aggregates by antigen mediation in the capture chamber; separating single microparticles and the aggregates by retaining only the aggregates in the capture chamber; dissociating the aggregates into single microparticles; and detecting, in the detection chamber, an amount of single microparticles obtained from dissociated aggregates.

In yet another aspect, the present invention provides a method for simultaneously detecting first and second antigens using a biosensor, the biosensor having a capture chamber and detection chamber which are separate from and in fluid communication with each other, the method including: applying a sample in the capture chamber, the sample containing the first and second antigens and first and second microparticles having antibodies immobilized on their surfaces; allowing the first and second microparticles to form respective first and second aggregates mediated by the first and second antigens, respectively, in the capture chamber; separating single first and second microparticles and the first and second aggregates by retaining only the first and second aggregates in the capture chamber; dissociating the first and second aggregates into single first and second microparticles by using an elution buffer; and detecting, in the detection chamber, an amount of single first and second microparticles obtained from dissociated first and second aggregates.

In yet another aspect, the present invention provides a microfluidic device forming a biosensor, which includes: a capture chamber, having a three-dimensional structure and antibodies immobilized on the three-dimensional structure; and a detection chamber separate from and in fluid communication with the capture chamber, the detection chamber having a detection device for detecting single microparticles passing through the detection chamber.

In yet another aspect, the present invention provides a microfluidic device forming a biosensor, which includes: a capture chamber; and a detection chamber separate from and in fluid communication with the capture chamber, the detection chamber having a detection device for detecting single microparticles and dimerized microparticles passing through the detection chamber, the detection device generating different signals upon detecting the single microparticles and the dimerized microparticles.

It is to be understood that both the foregoing general description and the following detailed description are exem-

DETAILED DESCRIPTION OF PREFERRED EMBODIMENTS

Embodiments of the present invention provide methods to improve immunoreaction efficiency by increasing the number of antibody per reaction volume in decoupled biosensors, which have a capture chamber and a separate detection chamber. In some embodiments of the present invention, in the capture chamber immunoreaction can occur under a condition of more than $5 \times 10^{-7}$ mol/L capture antibody concentration.

Two types of reactions may be used in the capture step, namely homogeneous reactions and heterogeneous reactions, described in more detail later. The embodiments shown in FIGS. 1(a)-5(B) use homogeneous reactions, and the embodiment shown in FIGS. 6(A)-6(B) use heterogeneous reactions.

The embodiments shown in FIGS. 1(A)-4 implement particle aggregation and size-separation mechanism in the capture chamber of the decoupled biosensor. The decoupled biosensor in this invention has a size-separation moiety between the capture chamber and the detection chamber.

To achieve aggregation, two or more types of antibodies can be used; or in an alternative embodiment, one type of antibody can be used. In the latter case (one type of antibody), the antigen should have more than two epitopes or should form multi-mers. The antibodies are immobilized onto microparticles, typically with more than two antibodies per microparticle. In the presence of the antigen, the microparticles form aggregations through antigen mediation. This aggregation reaction is conducted in the capture chamber of the decoupled biosensor. After aggregation reaction in the capture chamber, reaction samples are transferred to the detection chamber. If the aggregation happens and the aggregation size is larger than the threshold which can pass through the size-separation mechanism, the aggregation is trapped and cannot pass through to the detection chamber. Then by using an elution buffer which can dissociate aggregated microparticles, aggregations are dissociated into single microparticles which can pass through the size-separation mechanism and go to the detection chamber. By detecting the dissociated single microparticles one-by-one using a device to measure a change in electrical impedance, the amount of antigen can be quantified or estimated.

Figure 5A:
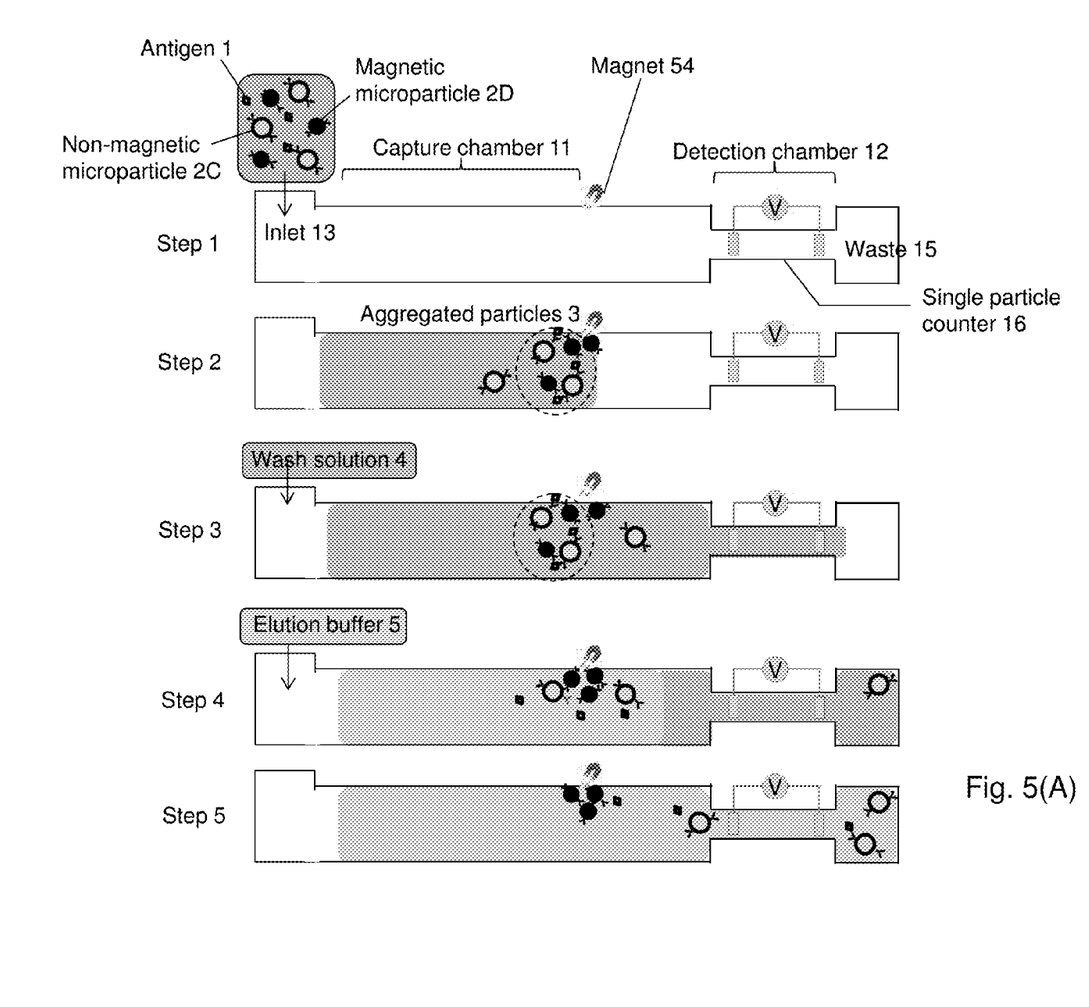
FIGS. 5(A) and 5(B) schematically illustrate a biosensor device and method using homogeneous capture and magnetic separation according to another embodiment of the present invention.
Figure 5B:
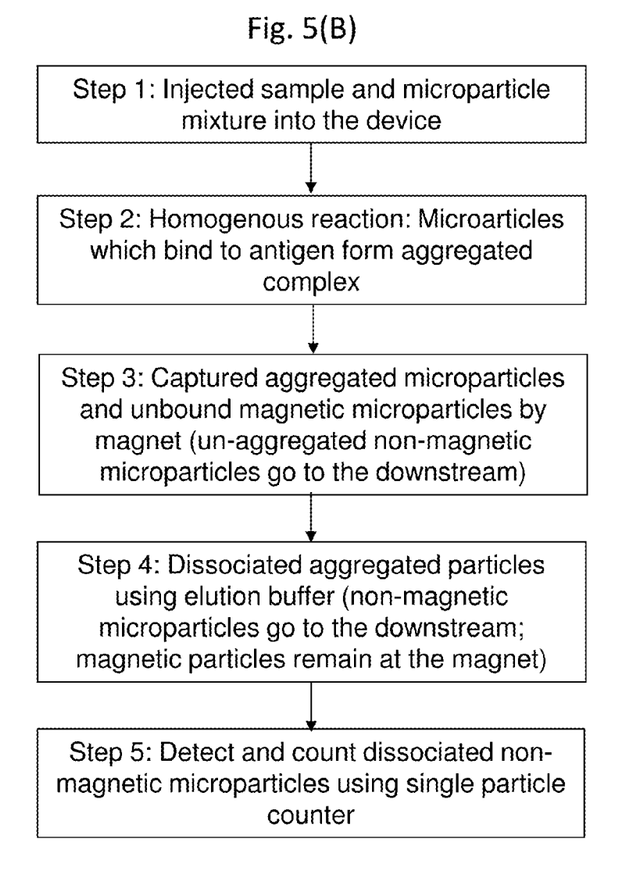

In the embodiments shown in FIG. 5, instead of the size-separation mechanism, magnetic force is used to separate bound (aggregated) and unbound (single) microparticles. In this case, two kinds of microparticles are used, including non-magnetic microparticles (microparticles that are not attracted by magnetic field) and magnetic microparticles which are attracted by magnetic field. A magnetic field is established in an area between the capture chamber and detection chamber. Different antibodies can be used for the non-magnetic microparticles and the magnetic microparticles respectively, or the same antibody can be used if the antigen has more than two epitopes or forms multi-mer. In the presence of the antigen, non-magnetic microparticles and magnetic microparticles form aggregations through antigen mediation. This aggregation reaction is conducted in the capture chamber of the decoupled biosensor. After aggregation reaction in the capture chamber, aggregated microparticles and unbound magnetic microparticles are trapped by the magnetic field, although unbound non-magnetic microparticles can continue downstream. Then by using an elution buffer which can dissociate aggregated microparticles, aggregations are dissociated into single microparticles, and dissociated non-magnetic microparticles go to the detection chamber. Magnetic microparticles remain in the magnetic field.

The microparticles may be made of a suitable material that can cause change in the electrical properties of the fluid so that they can be detected by the detection device in the detection chamber. Examples include polymer particle, such as polystyrene particles or beads, metal colloids, etc. Methods for making such microparticles are known in the field. See, for example, US 2011/0312518, para. [0140].

The embodiments are described in more detail below with reference to the drawings.

Figure 1A:
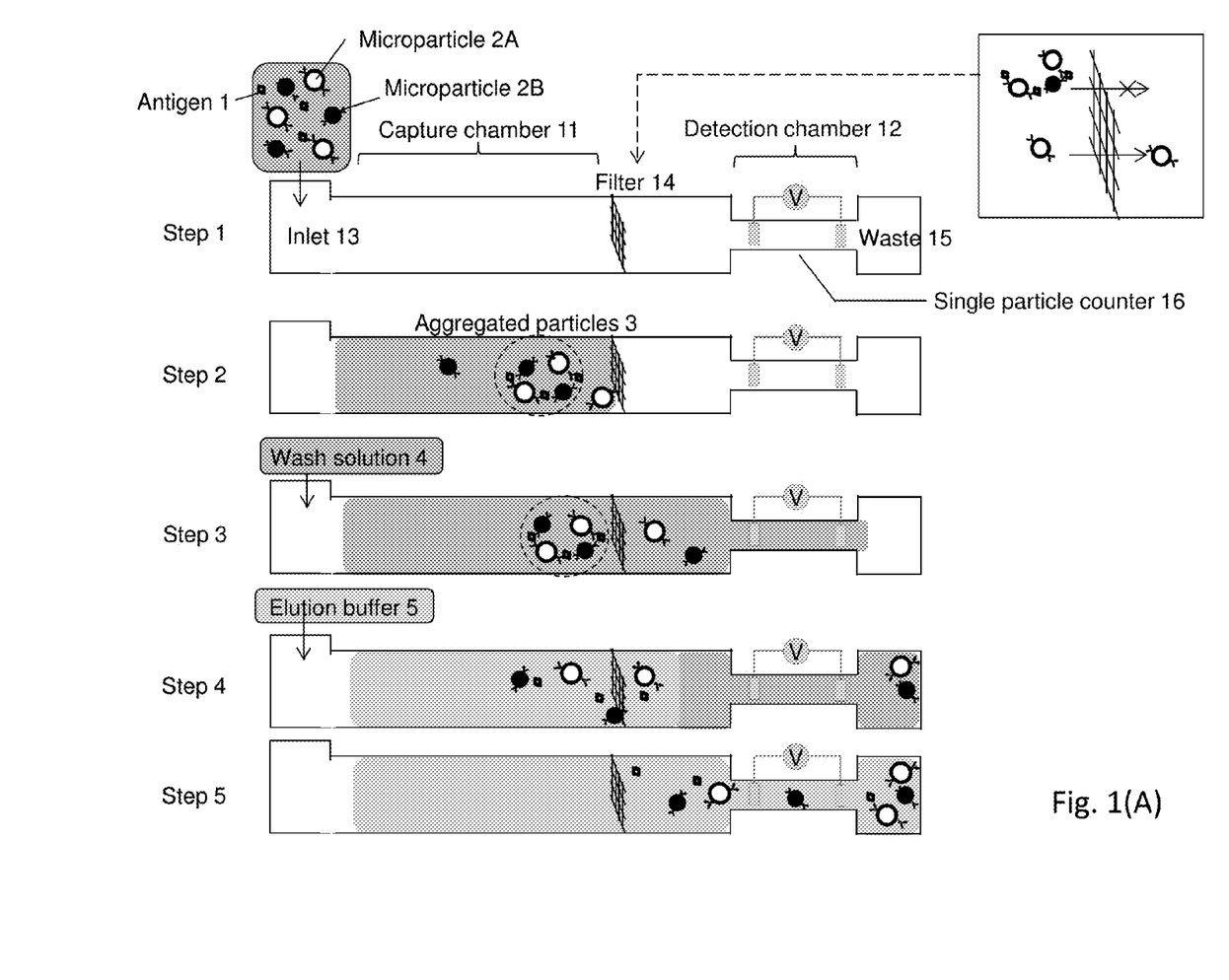
FIGS. 1(A) and 1(B) schematically illustrate a biosensor device and method using homogeneous capture (aggregation) and size separation according to an embodiment of the present invention.
Figure 1B:
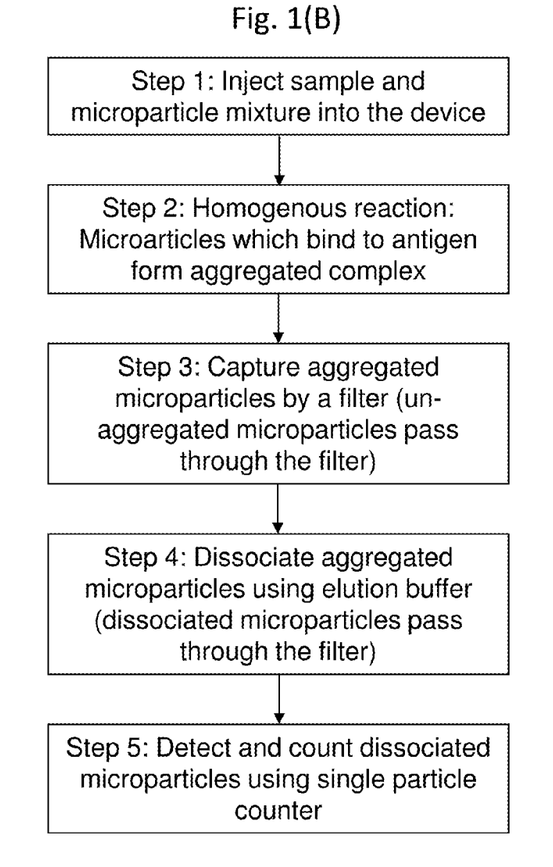

FIGS. 1(A) and 1(B) schematically illustrate a biosensor device and method based on homogeneous capture (aggregation) according to a first embodiment of the present invention. This embodiment uses size filtration to separate bound and unbound microparticles. As shown in FIG. 1(A), the biosensor is a microfluidic device which has a capture chamber 11 with an inlet 13, a detection chamber 12, and a waste channel 15 with an outlet (not shown). The detection chamber 12 is a micro channel where only single microparticle can pass through, and has a voltage applied to its two ends to measure a change in electrical impedance, forming a single particle counter 16, similar to that described in Mok et al. PNAS 2014, and US 2011/0312518 (see [0146], [0184], [0298]-[0303], FIGS. 4, 26, 27). A filter 14 having a predetermined pore size is provided between the capture chamber 11 and the detection chamber 12; the filter can pass single microparticles but stops aggregated microparticles.

FIGS. 1(A) and 1(B) illustrate five steps of the detection method. In Step 1, a sample solution containing an antigen 1 (biomolecules to be detected, also referred to as analyte) and two types of microparticles 2A and 2B is injected via the inlet 13 into the capture chamber 11 of the biosensor. The two types of microparticles 2A and 2B have two respective types of antibodies attached on their surfaces; both types of antibodies bind to the antigen 1. The two types of microparticles themselves may be the same except for the different antibodies. The concentration of microparticles in the sample is controlled so as to give a satisfactory reaction rate. As mentioned earlier, an antibody concentration of $5 \times 10^{\wedge}-7$ mol/L is desired so that the reaction in the capture chamber can be substantially completed within 10 min.

Note that in this embodiment, the microparticles with antibodies are mixed in the sample solution injected into the biosensor at the time of use. Alternatively, microparticles with antibodies can be provided in the capture chamber before sample injection; i.e., the biosensors that are provided to the users already contain microparticles with antibodies in the capture chamber. The alternative approach is more convenient for the users, but the antibodies' stability might be a concern.

In Step 2, microparticles (both types 2A and 2B) bind to antigens 1 and form aggregated complexes 3. This type of reaction, where the antibodies, being attached to the microparticles, are free in the sample solution (as opposed to being immobilized in the capture chamber), is referred to as a homogenous reaction. The reaction is allowed to proceed for a period of time. In Step 3, a wash solution 4 is applied to the capture chamber 11 to wash unbound microparticles through the filter 14. The pore size of the filter 14 is designed so that unbound single microparticles 2A, 2B pass through the filter while aggregated complexes 3 formed by multiple microparticles do not and are captured by the filter.

Then, in Step 4, an elution buffer 5 is injected into the capture chamber 11 via the inlet 13. The elution buffer 5 contains substances that dissociate the aggregated microparticles 3, and the resulting single microparticles 2A, 2B pass through the filter 14. In Step 5, the dissociated microparticles 2A and 2B, having passed through the filter 14, are counted in the detection chamber 12 by the single particle counter 16.

The technique employed in this embodiment solves the challenge of how to separate bound and unbound microparticles.

The antibodies on the microparticles are typically an order of 100 times smaller than the microparticles. Multiple antibodies are typically present on the surface of each microparticle. Because each of the two types of microparticles can bind to the antigen (at two respective sites simultaneously), the aggregate of microparticles tend to form long chains, which can have branches. In the detection step (Step 5), there is no need to discriminate between the two types of microparticles 2A and 2B. Although there is not an exact relationship between the total number of single microparticles counted in Step 5 and the number of antigens, the amount of antigens can be estimated from the number of microparticles counted.

Figure 2A:
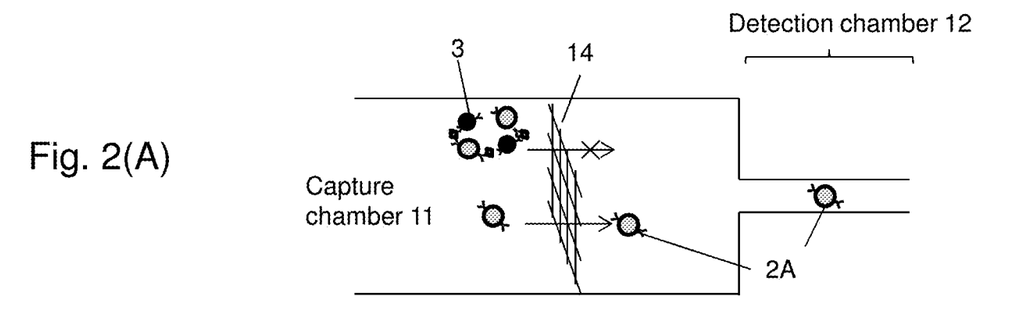
FIGS. 2(A)-(D) schematically illustrate variations of the embodiment of FIG. 1.
Figure 2B:
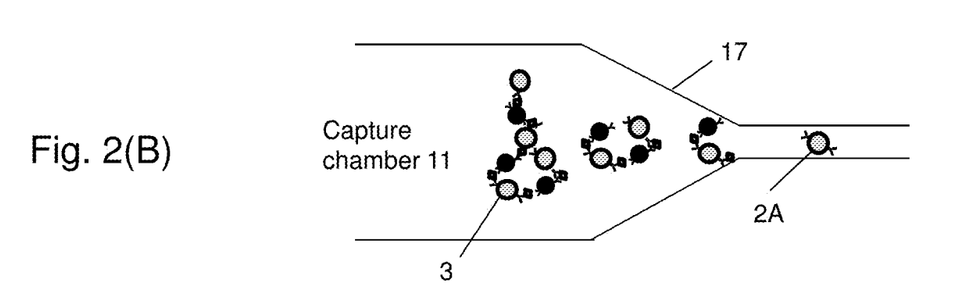
Figure 2C:
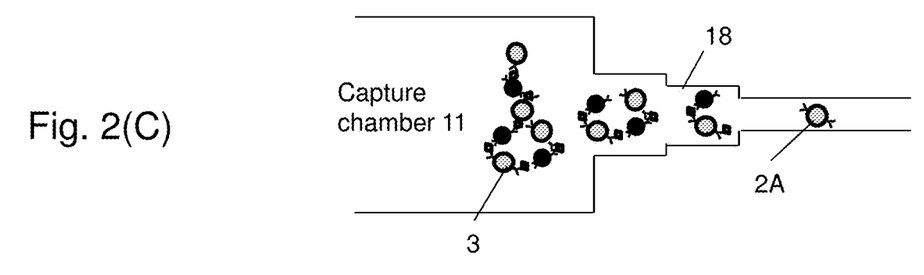
Figure 2D:
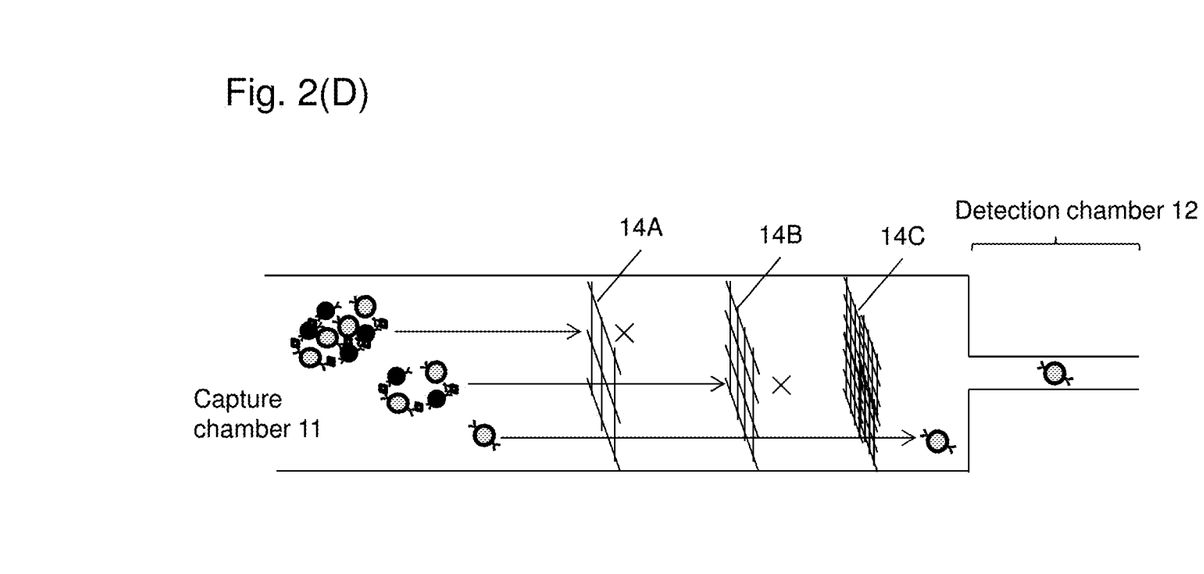

FIGS. 2(A)-2(D) schematically illustrate variations of the first embodiment, using size filtration for separation. FIG. 2(A) shows a devise using a filter 14 to separate aggregated and un-aggregated microparticles, as in the embodiment of FIG. 1. FIG. 2(B) shows a device using a continuously tapered channel 17 between the capture chamber 11 and the detection chamber 12 for separating the aggregated and un-aggregated microparticles. FIG. 2(C) shows a device using a step-wise tapered channel 18 between the capture chamber 11 and the detection chamber 12 for separating the aggregated and un-aggregated microparticles. FIG. 2(D) shows a device using a cascade of filters 14A-C gradually reducing in pore size for separating the aggregated and un-aggregated microparticles. In the structure of FIG. 2(D), the first filter 14A (largest pore size) allows some smaller aggregated microparticles to pass through, while the last filter 14C (smallest pore size) only allows single microparticles to pass through. This design reduces clogging of the filters.

The operations of the variations shown in FIGS. 2(A)-2(D) are similar to the embodiment shown in FIG. 1(A), where the tapered shapes 17, 18 and the cascading filters perform similar functions as the filter in FIG. 1(A).

Figure 3:
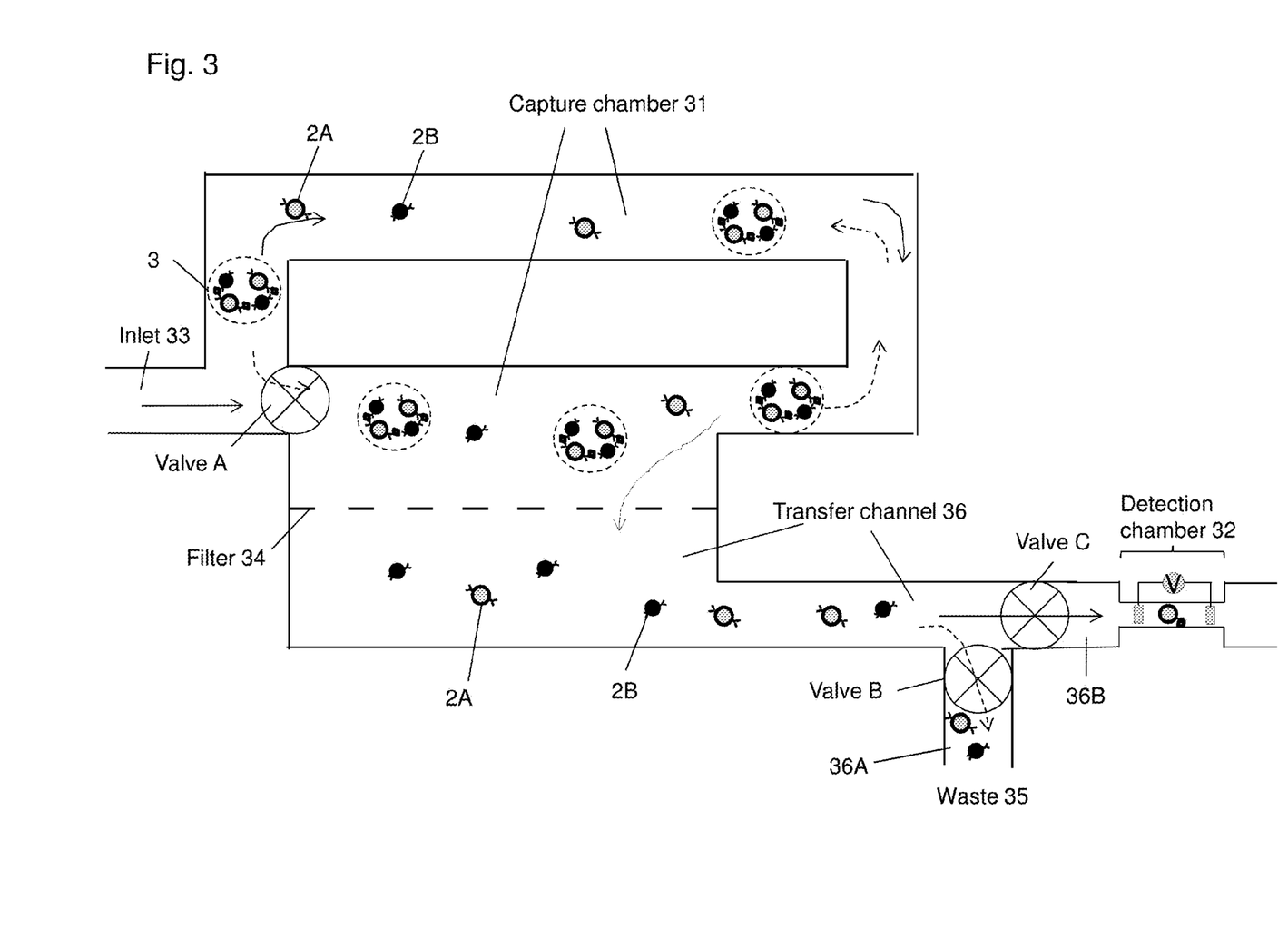
FIG. 3 schematically illustrates a biosensor device and method using cross flow filtration according to another embodiment of the present invention.

FIG. 3 schematically illustrates a biosensor device and method according to another embodiment of the present invention, based on homogeneous reaction and size filtration, using cross flow filtration. The microfluidic device has a capture chamber 31 which has a looped shape. A valve A is located along the loop path of the capture chamber 31, near the inlet 33. A filter 34 is provided between the capture chamber 31 and a transfer channel 36; unbound (singe) microparticles 2A, 2B can pass through the filter 34 while aggregated complexes 3 cannot. The filter 34 may be provided at a wider interface area between the capture chamber 31 and the transfer channel 36 to increase the filter area. The transfer channel 36 has two branches; one branch is controlled by a valve B and leads to a waste reservoir 35, and the other is controlled by a valve C and leads to the detection chamber 32.

In operation, after a sample solution containing the antigen and the two types of microparticles are introduced to the capture chamber 31 via the inlet 33, with valve A open and valves B and C closed, the immunoreaction is allowed to proceed for a period of time. Then, with valve A open, valve B open, and valve C closed, a wash solution is applied to the capture chamber 31 to wash unbound microparticles through the filter 34, so as to separate aggregated microparticles and single microparticles. The fluid flows in the looped part of the capture chamber 31, in a counter-clockwise direction in this example, and the unbound microparticles flow through the filter 34 and is discharged via valve B into the waste reservoir 35 (as schematically indicated by the dashed-line arrows in FIG. 3).

Thereafter, valve A is closed, valve B is closed, and valve C is open; an elution buffer is injected into the capture chamber 31 via the inlet 33 and flows through it in the looped part of the capture chamber, in the clockwise direction in this example. The aggregated microparticles are dissociated, and the dissociated microparticles pass though valve C to the detection chamber 32 to be detected (as schematically indicated by the solid-line arrows in FIG. 3).

In this embodiment, the filter 34 is oriented along a side plane of the looped part of the capture chamber so that when the fluid circulates in the looped part of the capture chamber 31, it flows in a substantially parallel direction over the surface of the filter, which helps to flush the filter 34 to prevent clogging, and promotes the capture reaction. Cross flow filtration methods per se are generally known.

Figure 4:
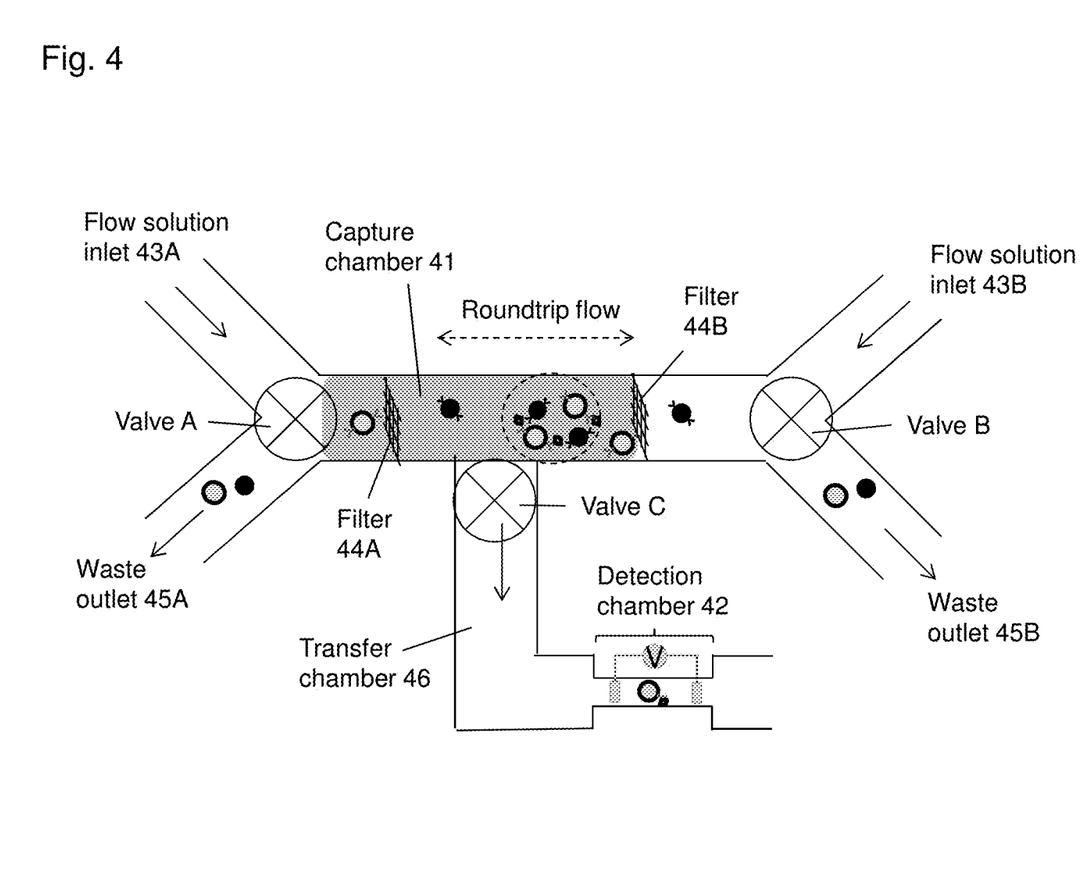
FIG. 4 schematically illustrates a biosensor device and method using roundtrip flow filtration according to another embodiment of the present invention.

FIG. 4 schematically illustrates a biosensor device and method according to another embodiment of the present invention, based on homogeneous reaction and size filtration, using a roundtrip flow. The microfluidic device has a capture chamber 41 with two filters 44A and 44B at its two ends. At each end of the capture chamber 41, beyond the respective filter, an inlet 43A/43B and an outlet branch 45A/45B are provided, with a valve (A and B, respectively) that opens/closes the respective inlet and outlet. The inlet at each end is for supplying a flow solution and the outlet at each end is for waste discharge. A transfer channel 46 is joined to the capture chamber 41 between the two filters 44A/44B, controlled by a valve C, and leads to the detection chamber 42.

In operation, after a sample solution containing the antigen and the two types of microparticles are introduced to the capture chamber 41 via one of the inlets, with valve C closed, the immunoreaction is allowed to proceed for a period of time. Then, valve C remains closed, and valves A and B are operated to alternately open and close the inlet 43A/43B and outlet 45A/45B at the two ends, and a wash solution is introduced through the two inlets. More specifically, during first time periods, valve A opens its associated inlet 43A and close its associated outlet 45A while valve B closes its associated inlet 43B and opens its associated outlet 45B, and the wash solution flows from left to right in the illustrated example; and during second time periods which alternate with the first time periods, valve A closes its associated inlet 43A and opens its associated outlet 45A while valve B opens its associated inlet 43B and closes its associated outlet 45B, and the wash solution flows from right to left. This creates a roundtrip flow pattern, and unbound microparticles are discharged with the wash solution via the outlets 45A and 45B. As a result, the aggregated microparticles and single microparticles are separated by the filters 44A and 44B. The roundtrip flow of the fluid in the capture chamber 41 helps to flush the filters 44A and 44B to prevent clogging.

Thereafter, valves A and B are controlled to close both outlets 45A and 45B, and to open one or both of the two inlets 43A and 43B, and valve C is open; an elution buffer is injected into the capture chamber via the open inlet(s). The aggregated microparticles are dissociated, and the dissociated microparticles pass though valve C to the detection chamber 42 to be detected.

FIGS. 5(A) and 5(B) schematically illustrate a biosensor device and method based on homogeneous capture and magnetic separation according to another embodiment of the present invention. As shown in FIG. 5(A), the microfluidic device is similar to that shown in FIG. 1(A), except that no filter is provided, but a magnetic field is applied to an area of the capture chamber 11 near the detection chamber 12, for example by using a magnet 54.

FIGS. 5(A) and 5(B) illustrate five steps of the detection method of this embodiment. In Step 1, a sample solution containing an antigen 1 and two types of microparticles 2C and 2D is injected via the inlet 13 into the capture chamber 11. The two types of microparticles have two respective types of antibodies attached on their surfaces; both types of antibodies bind to the antigen. One type of microparticles 2D is magnetic, the other type 2C is non-magnetic.

In Step 2, microparticles (both types, 2C and 2D) bind to antigens 1 and form aggregated complexes 3. The reaction is allowed to proceed for a period of time. In Step 3, a wash solution 4 is applied to the capture chamber 11 to wash unbound non-magnetic microparticles 2C out of the capture chamber. Both the aggregate microparticle complexes 3, which contain the magnetic type of microparticles 2D, and the unbound magnetic microparticles 2D are retained in the area of the capture chamber 11 where the magnetic field is present.

Then, in Step 4, an elution buffer 5 is injected into the capture chamber 11 via the inlet 13. The elution buffer 5 dissociates the aggregated microparticles 3. The dissociated non-magnetic microparticles 2C are no longer retained by the magnetic field. In Step 5, the non-magnetic microparticles 2C flow through the detection chamber 12 and are counted by the single particle counter 16. The amount of antigens 1 can be estimated from the number of microparticles counted.

The magnetic microparticles 2D remain in the capture chamber 11 in Step 5; they can be released later by removing the magnetic field.

Figure 6A:
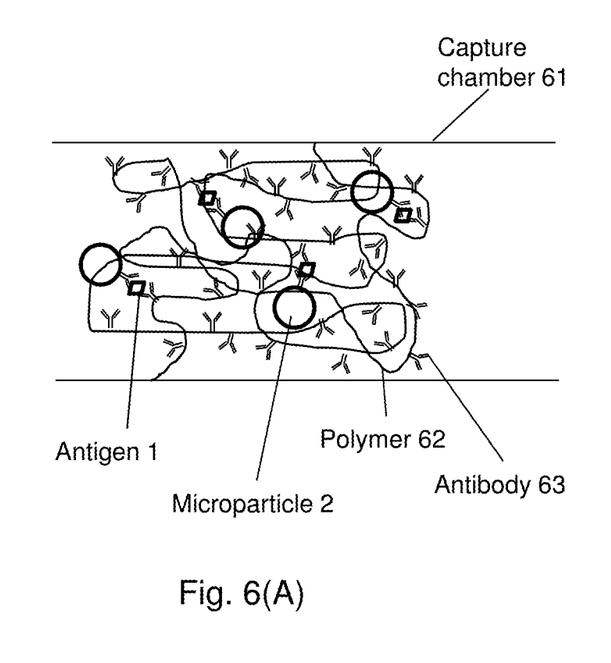
FIGS. 6(A)-6(B) schematically illustrate biosensor devices and methods according to other embodiments of the present invention, which implement 3-dimensional structures for antibody immobilization.
Figure 6B:
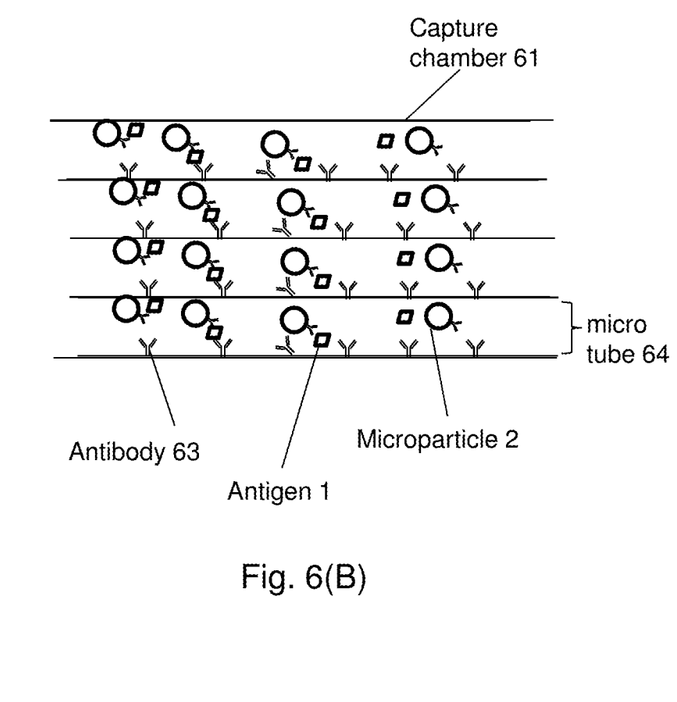

FIGS. 6(A)-6(B) schematically illustrate a biosensor device and method according to other embodiments of the present invention, which implement 3-dimensional structures for antibody immobilization within the detection chamber. The 3-d structure can be a polymer material (FIG. 6(A)) or plurality of micro size tubes (FIG. 6(B)). By using 3-d structure for antibody immobilization, the number of antibodies for immunoreaction per volume within the capture chamber can be increased.

FIGS. 6(A)-6(B) show a part of the capture chamber of a decoupled biosensor of these embodiments. The other parts of the biosensor, including the detection chamber, are similar to those shown in the embodiment of FIG. 1. The capture chamber 61 has antibodies 63 immobilized in a volume of the capture chamber, forming a 3-d structure.

In FIG. 6(A), the 3-d structure is formed by a polymer material 62 immobilized in the capture chamber 61, and attached along the polymer chains are antibodies 63 which bind to the antigen 1. The polymer material 62 may be any suitable solid polymers, such as hydrophilic polymer, carboxyl methyl dextran (CMD), polyethylene glycol (PEG), poly(acrylic acid), poly(methacrylic acid), etc. Using the polymers 62 in the capture chamber 61 increases the antibody binding sites per volume. No filter is required between the capture chamber and the detection chamber. In operation, a sample containing the antigen 1 and microparticles 2 (only one type is needed) with antibodies is introduced to the capture chamber 61, as shown in FIG. 6(A). The antibodies on the microparticles 2 and the antibodies on the polymer material 62 bind to two different sites of the antigen 1. Through antigen mediation, the microparticles are captured by the antibodies 63 immobilized onto the 3-d structure 62 in the capture chamber 61. This type of reactions, where antibodies 63 are immobilized in the capture chamber 61, is referred to as heterogeneous reactions. After a period of time, a wash solution is applied to the capture chamber 61 to wash away the unbound microparticles 2, and then an elution buffer is added to the capture chamber 61 to dissociate the microparticles 2 from the polymer 62. The dissociated single microparticles 2 move to the detection chamber to be counted, so that the amount of antigen 1 can be quantified or estimated.

In FIG. 6(B), the 3-D structure of the capture chamber 61 is formed by forming a plurality of micro tubes 64, with antibodies 63 immobilized on the surface of the micro tubes. The diameter of the micro tubes 64 should be larger than the microparticles 2. Preferably, the total volume of the micro tubes 64 depends on the sample volume. This structure increases the antibody binding sites per volume of the capture chamber 61. No filter is required between the capture chamber 61 and the detection chamber. The operation of this biosensor is otherwise similar to the one in FIG. 6(A).

Figure 7A:
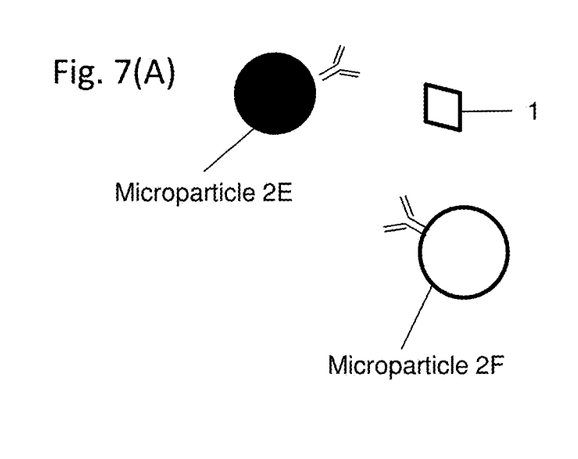
FIGS. 7(A)-(C) schematically illustrate a biosensor device and method according to another embodiment of the present invention.
Figure 7B:
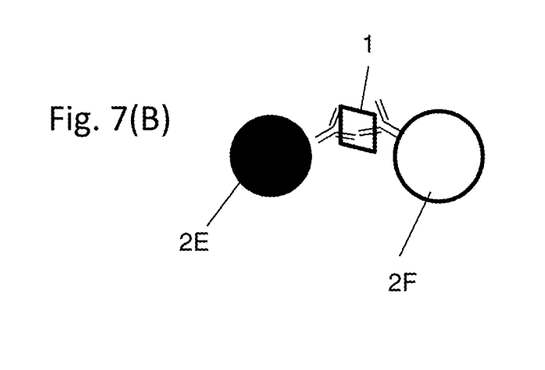
Figure 7C:
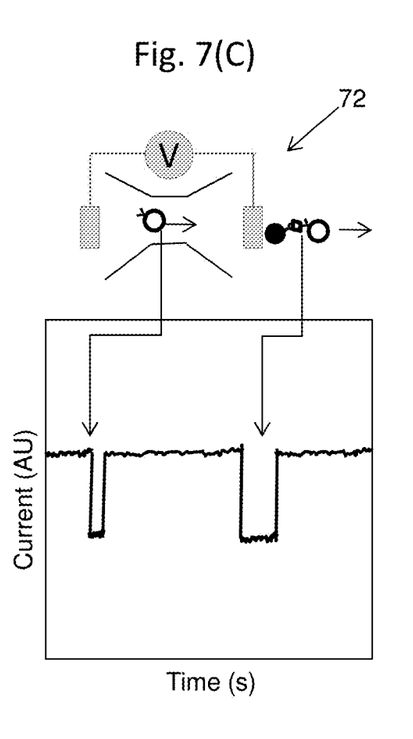

FIGS. 7(A)-(C) schematically illustrate a biosensor device and method according to another embodiment of the present invention, which uses microparticles to form dimers. Two types of antibodies are used; each microparticle has only one antibody on it, either the first type or the second type. I.e., there are two types of microparticles, and they form dimmers (one of each type of microparticle) in the presence of the antigen. FIG. 7(A) schematically shows two microparticles of two types, 2E and 2F, and the antigen 1. FIG. 7(B) schematically shows the dimer they form. Alternatively (not shown), the antigen 1 is one that has two epitopes or form dimers, and only one type of microparticle with one type of antibody is used; two microparticles each having one antibody form a dimer in the presence of the antigen. This is a type of homogeneous reaction where the antibodies are free in the sample solution.

The biosensor of this embodiment has a structure similar to that shown in FIG. 1(A), having a capture chamber and a detection chamber, but without any filter between the two chambers. As shown in FIG. 7(C), the detection chamber 72 is sized so that the dimers can pass through it, and the single particle counter is designed so it can discriminate between single microparticles and dimerized microparticles based on the pulse width of the electrical signal. The number of antigens 1 can be quantified based on the number of dimers detected. This embodiment does not require size separation.

Figures 8A, 8B:
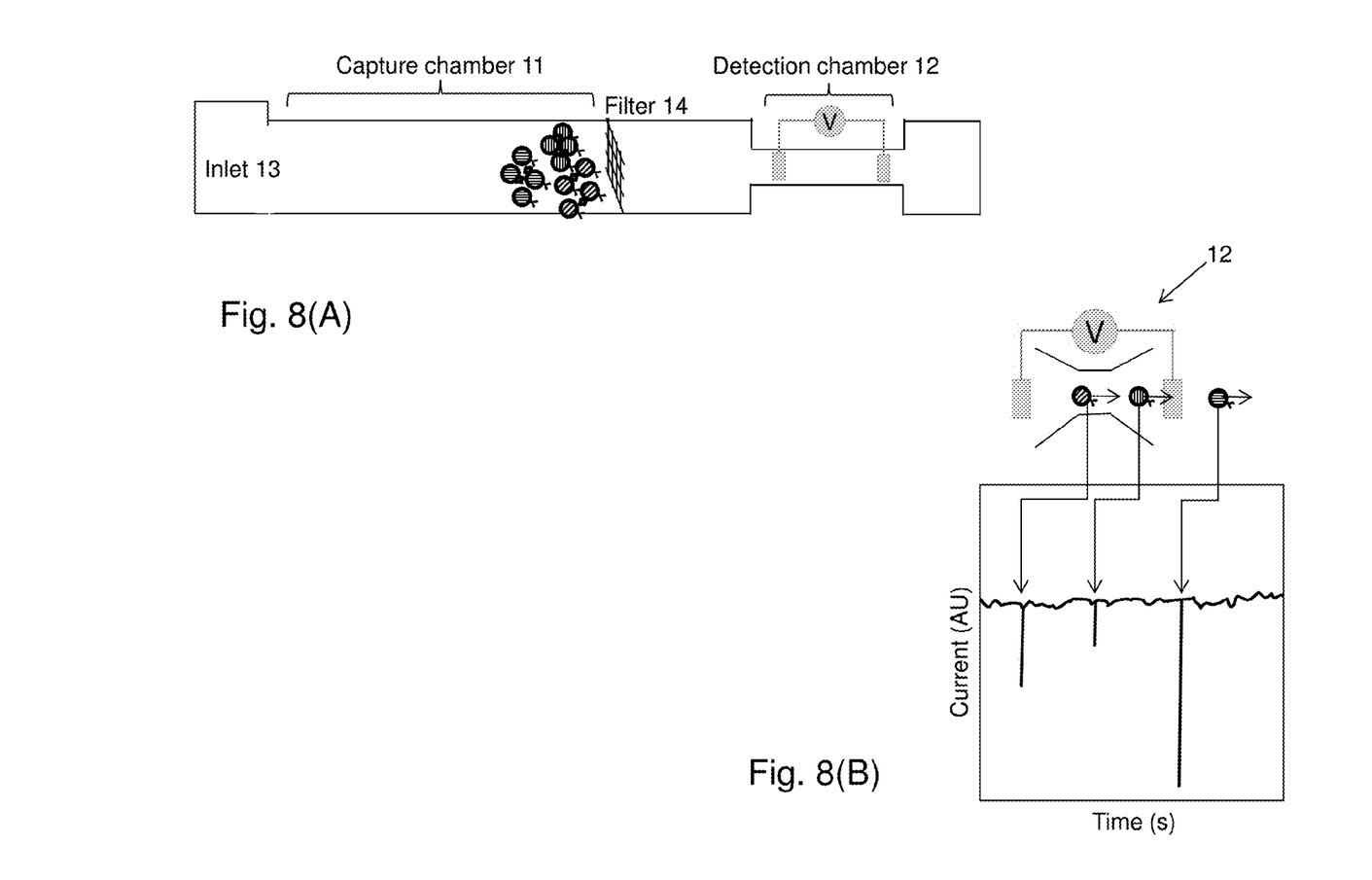
FIGS. 8(A) and 8(B) schematically illustrate a biosensor device and method according to yet another embodiment of the present invention, which is capable of detecting multiple types of antigens simultaneously present in a sample.

FIGS. 8(A) and 8(B) schematically illustrates another embodiment of the present invention, which is capable of detecting multiple types of antigens simultaneously present in a sample. Multiple types of microparticles are provided, where the different types of microparticles have different antibodies on them that bind to different types of antigens. The different types of microparticles also affect electrical impedance differently in the single particle counter of the detection chamber. For example, they may generate pulses of different magnitudes in the detected electrical current.

The working principle with respect to each antigen is similar to that of the embodiment of FIG. 1(A). In other words, for each antigen, two types of microparticles are provided in the sample, and they aggregate in the presence of that antigen. FIG. 8(A) schematically illustrates three different antigens and respective different types of microparticles. Note that for simplicity, the two types of microparticles for each antigen are not differentiated in this drawing. The elution buffer used contains substances that can dissociate all microparticles from their respective antigens.

The two types of microparticles that correspond to the same antigen give rise to the same electrical signal. Microparticles that correspond to different antigens give rise to different electrical signals, such as pulses of different magnitude (see FIG. 8(B)). Thus, the number of single microparticles corresponding to each antigen can be separately counted. Using this technique, multiplexing biosensing (detection of multiple antigens in the same sample) can be realized.

The structure of the biosensor in the embodiment of FIG. 8(A) is similar to that of the embodiment of FIG. 1(A), with a capture chamber 11, a detection chamber 12, and a filter separating 14 the two. The multiplexing technology can also be applied to the embodiments shown in FIGS. 2(A)-7; in fact, it can be applied to any microfluidic biosensors with decoupled capture chamber and detection chamber, including that described in the Mok et al., PNAS 2014 article, which uses the type of single particle counter that can differentiate the different types of microparticles.

In practice, the reaction rate of an immunoreaction can be calculated as follows:

$$\text{Reaction rate (\%): } X/[Ag_0] * 100$$

$$X = \frac{\alpha \cdot \beta \{1 - \exp(\alpha \cdot k_{on} \cdot t)\}}{\beta - \alpha \cdot \exp(\alpha \cdot k_{on} \cdot t)}$$

$$p = [Ab] + [Ag] + k_{off}/k_{on}$$

$$q = [Ab] * [Ag]$$

$$a = \sqrt{p^2 - 4q}$$

$$\alpha = (p + a)/2$$

$$\beta = (p - a)/2$$

In one example, the following parameters are used in the calculation: antigen (Ag) concentration=1 ng/mL; Ag molecular weight=50 kDa; $k_{on}=10^{\wedge}6$; $k_{off}=10^{\wedge}-4$; antibody [Ab] concentration>$5 \times 10^{\wedge}-7$ mol/L. This antibody concentration is the concentration above which almost 100% of the antigens are captured within 10 min (using ka=$10^{\wedge}6$, kd=$10^{\wedge}-4$). It can be seen that antibody concentration plays an important role in increasing reaction speed in the capture chamber of a biosensor.

It will be apparent to those skilled in the art that various modification and variations can be made in the biosensor devices and related methods of the present invention without departing from the spirit or scope of the invention. Thus, it is intended that the present invention cover modifications and variations that come within the scope of the appended claims and their equivalents.

What is claimed is:

1. A microfluidic device forming a biosensor, comprising:
a capture chamber forming a loop including a first segment;
an inlet coupled to the loop of the capture chamber;
a first valve located on the loop between the inlet and the first segment of the loop;
a filter located on a side plane of the first segment of the loop parallel to a flow direction of the capture chamber, configured to separate aggregations of microparticles and single microparticles;
a transfer channel having a second segment in fluid communication with the first segment of the capture chamber via the filter, the transfer channel further having a first branch and a second branch;
a detection chamber coupled to the first branch of the transfer channel, the detection chamber having a detection device configured to detect the single microparticles passing through the detection chamber;
a second valve located on the first branch of the transfer channel between the second segment and the detection chamber; and
a third valve located on the second branch of the transfer channel.

2. The microfluidic device of claim 1, wherein when the first and second valves are open and the third valve is closed, and a wash solution is injected through the inlet, the single microparticles are washed through the filter to the second branch of the transfer channel; and when the first and second valves are closed and the third valve is open, and an elusion buffer is injected through the inlet, the aggregated microparticles are dissociated and the dissociated single microparticles pass though the filter and the third valve to enter the detection chamber to be detected.

3. A microfluidic device forming a biosensor, comprising:
a capture chamber;
a first inlet and a first outlet coupled to a first location of the capture chamber, and a first valve located at the first location of the capture chamber configured to either open the first inlet, or open the first outlet, or close both;

a second inlet and a second outlet coupled to a second location of the capture chamber, and a second valve located at the second location of the capture chamber configured to either open the second inlet, or open the second outlet, or close both;

two filters disposed in the capture chamber between the first and second locations, defining first segment of the capture chamber between the two filters, each configured to separate aggregations of microparticles and single microparticles;

a transfer channel coupled to the first segment of the capture chamber, and a third valve configured to open or close the transfer channel; and a detection chamber coupled to the transfer channel, the detection chamber having a detection device configured to detect single microparticles passing through the detection chamber.

4. The microfluidic device of claim 3, wherein when the third valve is closed and the first and second valves alternatingly either open the first inlet and the second outlet or open the second inlet and the first outlet, and a wash solution is injected through the inlet that is open, the single microparticles are washed out of the first segment of the capture chamber through the two filters; and when the third valve is open, the first and second valves close both the first and second outlet and opens one of the first or second inlets, and an elusion buffer is injected through the inlet that is open, the aggregated microparticles are dissociated and the dissociated single microparticles pass though the third valve to enter the detection chamber to be detected.

* * * * *